United States Patent [19]

Katzir et al.

[11] Patent Number: 4,482,424

[45] Date of Patent: Nov. 13, 1984

[54] METHOD FOR MONITORING ETCHING OF RESISTS BY MONITORING THE FLOURESENCE OF THE UNETCHED MATERIAL

[75] Inventors: Abraham Katzir, Afeka, Israel; Paul R. Kolodner, Maplewood, N.J.

[73] Assignee: AT&T Bell Laboratories, Murray Hill, N.J.

[21] Appl. No.: 492,433

[22] Filed: May 6, 1983

[51] Int. Cl.³ .......................................... H01L 21/306
[52] U.S. Cl. ................................... 156/626; 156/643; 156/652; 156/654; 156/668; 156/904
[58] Field of Search ............... 156/626, 627, 643, 652, 156/668, 654, 904

[56] References Cited

U.S. PATENT DOCUMENTS

| | | | |
|---|---|---|---|
| 4,244,799 | 1/1981 | Fraser et al. | 156/643 |
| 4,246,060 | 1/1981 | Keller | 156/627 |
| 4,377,436 | 3/1983 | Donnelly et al. | 156/626 |
| 4,394,237 | 7/1983 | Donnelly et al. | 156/643 |
| 4,415,402 | 11/1983 | Wang et al. | 156/626 |

FOREIGN PATENT DOCUMENTS

| | | | |
|---|---|---|---|
| 62302 | 10/1982 | European Pat. Off. | 156/627 |
| 26438 | 2/1982 | Japan | 156/626 |
| 47874 | 3/1982 | Japan | 156/627 |

*Primary Examiner*—Jerome Massie
*Attorney, Agent, or Firm*—Peter A. Businger; Bruce S. Schneider; Bernard Tiegerman

[57] ABSTRACT

A method for lithographically fabricating devices is disclosed. In accordance with the method, a sacrificial coating material (SCM), e.g., a resist, mixed with a fluorescent material is deposited onto a substrate and then etched. SCM etching is monitored by subjecting the fluorescent material within the SCM to fluorescence-inducing energy, and detecting the resulting fluorescence. Because the fluorescent material is etched away as the SCM is etched, fluorescence intensity decreases as SCM thickness is reduced. Thus, SCM etch end point is accurately determined because etch end point corresponds to the point in time when the detected fluorescence ceases.

16 Claims, 5 Drawing Figures

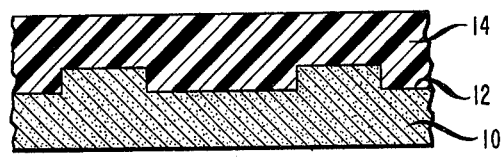
FIG. 1
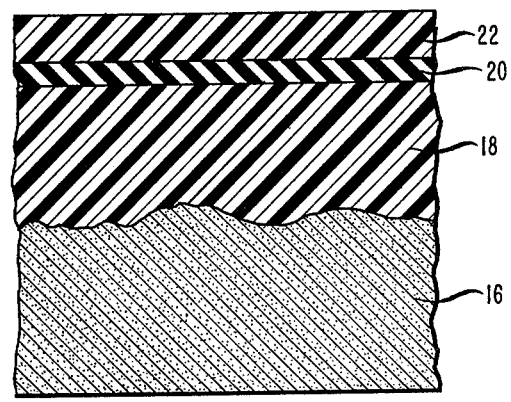
FIG. 2
FIG. 4
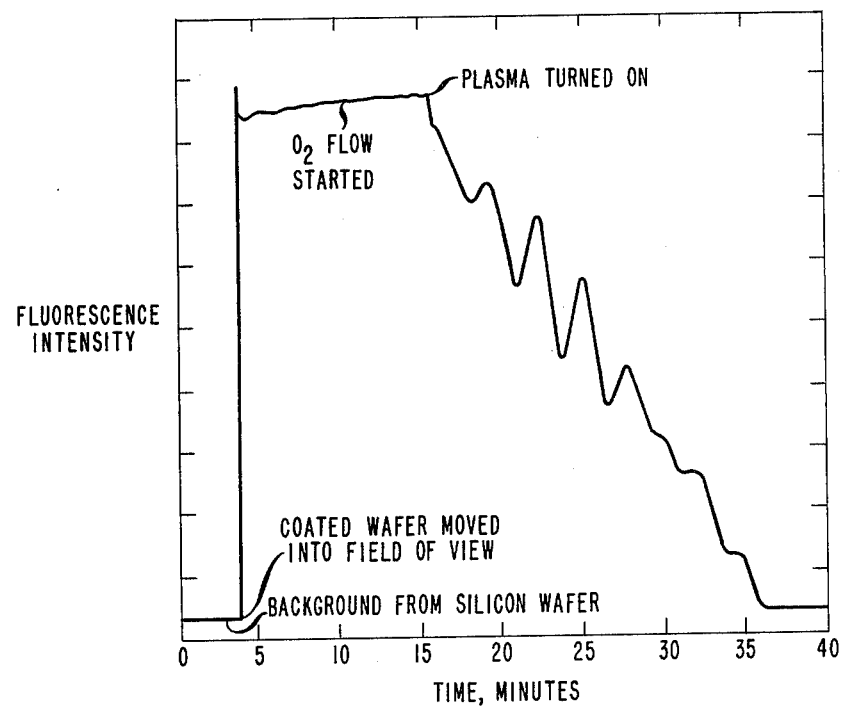

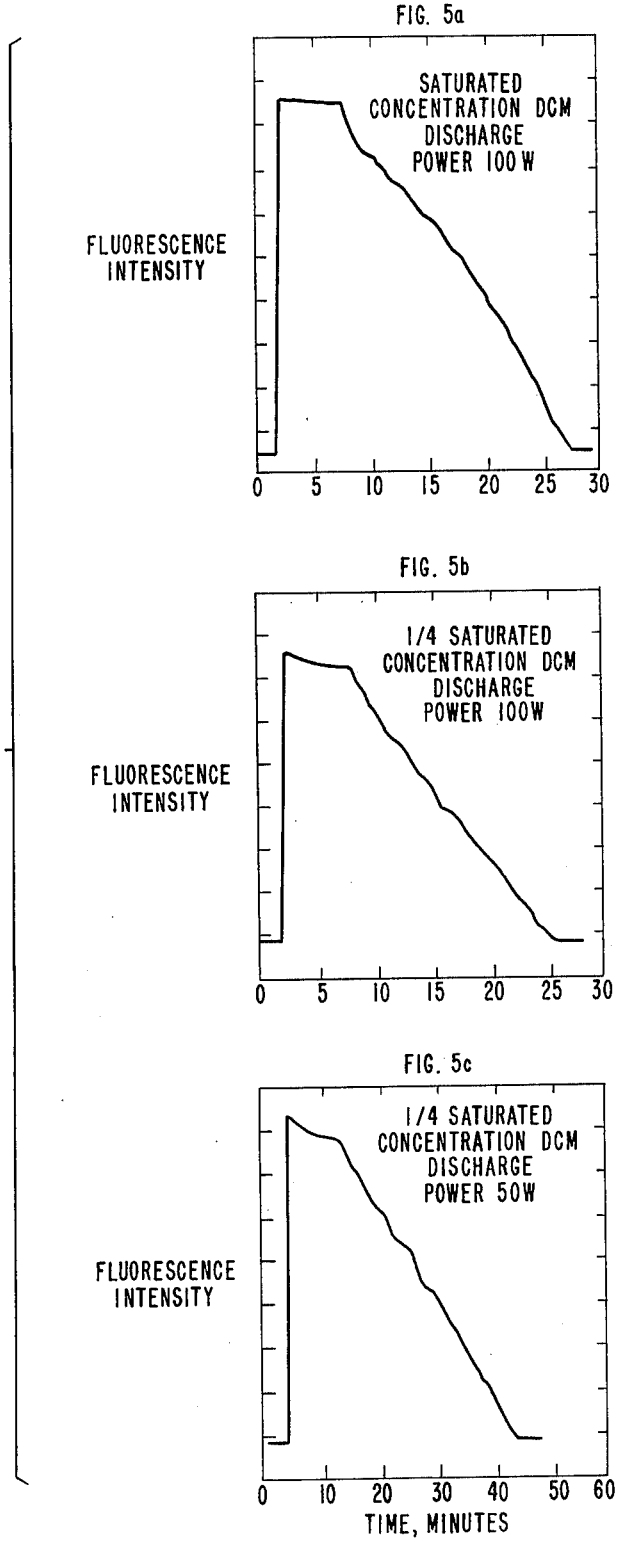

METHOD FOR MONITORING ETCHING OF RESISTS BY MONITORING THE FLOURESENCE OF THE UNETCHED MATERIAL

BACKGROUND OF THE INVENTION

1. Field of the Invention

The invention pertains generally to lithographic processes for producing devices such as, e.g., semiconductor devices and, more particularly, to a method for monitoring the etch depth and each end point of a resist undergoing etching (development).

2. Art Background

Lithographic processes play an important role in the manufacture of devices such as, e.g., semiconductor devices. During the manufacture of these devices lithographic processes are used to pattern substrates, such as, e.g., silicon wafers or processed silicon wafers which are, for example, wholly or partially covered by metal, silicon dioxide or polysilicon. Typically, a substrate is patterned by coating the substrate with an energy-sensitive material called a resist. Selected portions of the resist are exposed to a form of energy which induces a change in the solubility of the exposed portions in relation to a given developing agent or etchant. The more soluble portions of the resist are then removed by etching (developing) the resist with a wet chemical etchant or by employing a dry etching process, e.g., plasma etching or reactive ion etching. The resulting pattern defined in the resist is then transferred into the underlying substrate by, for example, etching or metallizing the substrate through the patterned resist.

An important consideration in the abovedescribed patterning procedure is the determination of the etch end point of the resist, i.e., the point in time when the resist has been etched through its thickness, and thus the interface between the resist and the underlying substrate has been reached. If, for example, the resist is being etched (developed) with a wet etchant which etches the resist both vertically (through its thickness) and laterally, then overetching the resist (subjecting the resist to the etchant for a longer period of time than is needed to etch through the thickness of the resist) will often result in excessive lateral etching of the resist. Such excessive lateral etching results in a loss of linewidth control during pattern transfer into the substrate. On the other hand, if the resist is being dry etched, e.g., reactive ion etched, then overetching will often result in the sputtering of the substrate, and the deposition of sputtered substrate material onto the walls of the patterned resist. Consequently, there will also be a loss of linewidth control during pattern transfer into the underlying substrate. Such losses of linewidth control are particularly significant if pattern feature sizes are a few micrometers or smaller.

Several different techniques have been used to monitor resist etch end point. Included among these are mass-spectrometric and optical interferometric techniques. In the former technique, mass-spectrometric analysis of, for example, an etching plasma is employed to determine resist etch end point. That is, for example, once a reaction product typical of the substrate is detected in the mass-spectrometric analysis of the plasma, then the interface between the resist and the substrate is assumed to have been reached, and etching is discontinued. While this technique is useful, the time resolution inherent in the analysis of reaction products, and thus the accuracy in the determination of the etch end point, is limited by the etch rate of the substrate and by the diffusion times of substrate reaction products to a detector. As a consequence, the determination of etch end point can be in error by up to several minutes. At typical plasma etch rates (of about 500 Angstroms per minute), such errors in the end point determination correspond to at least several hundred Angstroms, and often several thousand Angstroms, of the resist film thickness (typically only 1-2 $\mu$m thick), which is a very significant fraction of the resist thickness, and thus a very significant error in the determination of etch end point.

With typical optical interferometric techniques, light is shined on the resist undergoing etching, and a portion of the reflected light is detected, and the intensity of the detected light is recorded. As is known, the intensity of the reflected light oscillates periodically with time (as resist thickness is reduced) because of successive constructive and destructive interferences between light rays reflected from the bottom of the grooves being etched into the resist and light rays reflected from the underlying interface between the resist and the substrate. Etch end point is generally detected by looking for sharp changes in slope, or sharp changes in the oscillation frequency, of the detected signal. But the slope of the output signal does not always change abruptly at the end point, particularly if the substrate has optical properties similar to those of the resist, i.e., if the index of refraction of the substrate is approximately equal to that of the resist. In this case, the etch end point may also be in error by an equivalent resist thickness of at least several hundred Angstroms, and often as much as several thousand Angstroms.

Thus, those engaged in the development of lithography have long sought, thus far without success, a technique for more accurately determining the etch end point of resists.

SUMMARY OF THE INVENTION

The invention involves a technique, more accurate than prior techniques, for determining the etch end point of a sacrificial coating material (SCM), e.g., a resist, which is to be etched. In accordance with this inventive technique, an SCM is doped (physically mixed) with a fluorescent material. During etching of the SCM, an area of the SCM, and thus the fluorescent dopant within that area, is exposed to fluorescence-inducing energy, and the resulting fluorescence is detected and its intensity is recorded. As the SCM is etched, the intensity of the fluorescence diminishes because the fluorescent material is also being removed (etched). At the instant that the SCM has been etched through its thickness (at which point the monitored fluorescence ceases because the fluorescent material in the area under consideration has been removed), there is a sharp change in the slope of the detected signal, denoting the etch end point. The inventive technique is capable of determining etch end point to an accuracy (in terms of an equivalent SCM thickness) smaller than about 100 Angstroms, and even smaller than about 10 Angstroms, and potentially (theoretically) even smaller than about 0.1 Angstroms.

BRIEF DESCRIPTION OF THE DRAWINGS

FIG. 1 is a cross-sectional view of a substrate whose non-planar surface has been covered by a thick SCM in preparation for the planarization etch process;

FIG. 2 depicts the structure of the tri-level resist;

FIGS. 4 and 5(a)-5(c) are recordings of the fluorescence intensity signals detected during the etching of the photoresist films described in Examples 1-4.

DETAILED DESCRIPTION

Figure 3:
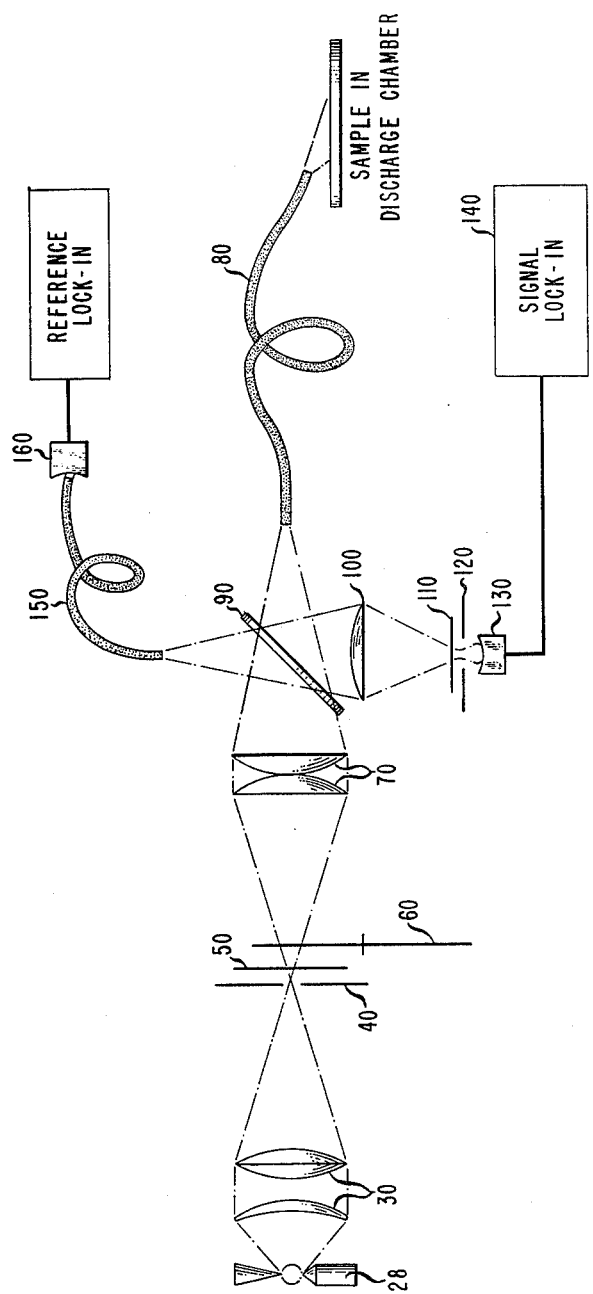
FIG. 3 is a schematic diagram of an optical system useful in the practice of the invention.

The invention is a method for fabricating devices, such as, e.g., semiconductor or magnetic bubble devices, which method involves the alteration, e.g., the patterning, of a substrate (such as, e.g., a silicon wafer or a processed silicon water which is, for example, wholly or partially covered by metal, silicon dioxide, or polysilicon). A substrate is altered, in accordance with the invention, by initially depositing a sacrificial coating material (SCM), e.g., a resist, which has been doped, i.e., physically mixed, with a fluorescent material, onto the surface of the substrate. The alteration of the substrate also includes the step of subjecting the deposited SCM to an etchant which etches away either all of the SCM or just selected portions of the SCM. For example, if the substrate is to be patterned, then the SCM which is employed is typically a resist. Selected areas of the resist are first exposed to a form of energy which either decreases (a positive resist) or increases (a negative resist) the solubility of the exposed portions in relation to a given developing agent or etchant. The more soluble portions of the resist are then etched away by, for example, wet chemical etching, plasma etching, or reactive ion etching the resist.

During the etching of the SCM, an area (or areas, or all) of the SCM is exposed to a form of energy which causes the fluorescent dopant within that area to fluoresce. A material is fluorescent, for purposes of the invention, if it emits electromagnetic radiation in response to an appropriate form of energy, e.g., light, electron beams, or ion beams. By monitoring the fluorescence of the dopant, the etch end point of the SCM, which corresponds to the point in time when the monitored fluorescence substantially ceases, is determined, and thus undesirable etching of the SCM and/or of the substrate is avoided. If the purpose of the etching is to create a pattern in the SCM which is to be transferred into the underlying substrate, then this is accomplished by, for example, etching or metallizing the substrate through the pattern SCM.

The inventive fabrication method encompasses processes for altering substrates other than conventional lithographic patterning processes. Included among these other processes is, for example, the planarization etch process described by A. C. Adams and C. D. Capio in "Planarization of Phosphorus-Doped Silicon Dioxide," *Journal of Electrochemical Society,* 128, pages 423-428 (February 1981). In the planarization etch process, and as shown in FIG. 1, a non-planar surface 12 of a substrate 10, which surface 12 is to be planarized (made substantially flat), is covered by a thick SCM 14, e.g., a thick layer of resist. The SCM 14 is chosen so that it etches at about the same rate as the substrate 10 in the presence of a particular etchant. By etching away the SCM, the substrate protrusions are also etched away, and thus a flat substrate surface is formed. In accordance with the invention, the planarization etch process proceeds as described above, except that the thick SCM 14 is doped (physically mixed) with a fluorescent material, and the fluorescence emitted by a portion (or portions) of doped SCM (in response to fluorescence-inducing energy) is monitored during the etching of the SCM. Once fluorescence ceases, etching is discontinued because all of the SCM will have been etched away, and a flat substrate formed without undesirable excessive etching of the substrate.

The invention also encompasses the use of SCMs which are comprised of several different material layers, one or more of which is doped with a fluorescent material, and whose fluorescence is monitored during etching to prevent undesirable etching of the substrate and/or of the different SCM layers. For example, the invention encompasses the tri-level resist process for patterning substrates, described by J. M. Moran and D. Maydan in "High Resolution, Steep Profile, Resist Patterns," *The Bell System Technical Journal,* 58 (5), pages 1027-1036 (May-June 1979), and also described in U.S. Pat. No. 4,244,799, issued to Fraser et al on Jan. 13, 1981. As depicted in FIG. 2, the tri-level resist includes a thick (typically 2 $\mu$m-thick), planarizing layer of organic material 18 deposited directly onto a substrate 16. In addition, the tri-level resist includes a thin (typically 1000 Angstroms thick) layer of $SiO_2$ 20 deposited onto the thick planarizing layer 18, as well as a thin (typically 4000 Angstroms thick), high resolution layer 22 of photoresist, x-ray resist, or electron beam resist deposited onto the $SiO_2$ layer 20. In practice, a pattern is initially defined in the upper, high resolution resist layer 22 by exposing and developing this layer. This pattern is then transferred into the $SiO_2$ layer 20 (using the high resolution resist layer 22 as an etch mask) by reactive ion etching the $SiO_2$ layer 20 in, for example, a $CHF_3$ plasma. Thereafter, the pattern in the $SiO_2$ layer 20 is transferred into the thick, planarizing layer 18 (using the patterned $SiO_2$ layer 20 as an etch mask) by reactive ion etching the planarizing layer 18 in, for example, an $O_2$ plasma.

The upper, high resolution resist layer 22 of the tri-level resist is often etched by the $CHF_3$ plasma used to etch the $SiO_2$ layer 20. Overetching the $SiO_2$ layer 20 produces undesirable excessive etching of the upper layer 22, and loss of linewidth control during pattern transfer from the upper layer 22 to the $SiO_2$ layer 20. In addition, overetching of the thick planarizing layer 18 often results in undesirable etching of the substrate 16 and/or sputtering of the substrate 16. Sputtering of the substrate 16 often results in deposition of sputtered substrate material onto the walls of the patterned planarizing layer 18, with consequential loss of linewidth control during pattern transfer into the substrate 16. To avoid these problems, and in accordance with the invention, the thick planarizing layer 18 is doped (physically mixed) with a fluorescent material, and the fluorescence emitted by an area (or areas) of the layer 18 (in response to fluorescence-inducing energy) is monitored during the patterning of the three layers 22, 20, and 18. During the reactive ion etching of the $SiO_2$ layer 20, in the $CHF_3$ plasma, the intensity of the fluorescence emitted by the planarizing layer 18 remains constant. But as soon as the detected fluorescence is first observed to substantially decrease (denoting the onset of the etching of the fluorescent material in the planarizing layer 18, and thus denoting the etch end point of the $SiO_2$ layer 20), the etching of the $SiO_2$ layer is halted. Thus, overetching of the $SiO_2$ layer 20, and undesirable excessive etching of the upper, high resolution resist layer 22, is avoided. In addition, during the patterning of the thick planarizing layer 18, when the monitored fluorescence substantially ceases (denoting that the fluorescent material has been entirely etched away, and thus the layer 18 has been etched through its thickness) etching of the layer 18 is halted. Consequently, undesirable etching or sputtering of the substrate 16 is avoided.

Typically, in the practice of the invention, an area (or areas, or all) of an SCM doped with a fluorescent material is subjected to a beam of fluorescence-inducing energy of power P, e.g., a beam of fluorescence-inducing electromagnetic radiation of power P (photons/second). If the fluorescent dopant (subjected to the fluorescence-inducing beam) absorbs only a fraction, $\theta$, of the incident fluorescence-inducing radiation, and if the dopant has a quantum efficiency $\eta_f$ (number of emitted photons/number of absorbed photons), then the number of photons emitted by the fluorescent material per unit time, $N_e$, is just $$N_e = P \cdot \theta \cdot \eta_f. \tag{1}$$

The emitted photons are typically collected by a photodetector whose output is measured by an electrical circuit with response time, $\Delta t$, i.e., whose output at any instant in time is the sum of all photons collected during the previous time increment, $\Delta t$. Generally, the detector will collect only a fraction, f, of the emitted photons during each of these time intervals, $\Delta t$ (the fraction, f, includes the fraction of the fluorescence collected by the detector, and includes interference effects). The photodetector will generally include a transducer, e.g., a photomultiplier (PM) tube, which converts the detected light signal into, for example, an electron current. If the PM tube has a quantum efficiency $\eta_c$ (number of emitted electrons/number of collected photons), then the measured fluorescence signal, N (the total number of electrons emitted by the PM tube, in response to the fluorescence, during each time interval $\Delta t$) is just $$N = P \cdot \theta \cdot \eta_f \cdot \eta_c \cdot \Delta t. \tag{2}$$

From Beer's law (see, e.g., Billings et al, eds. *American Institute of Physics Handbook* (McGraw-Hill, New York, 1972) p. 6–2), it follows that the absorption fraction, $\theta$ (in Equation (2)), is given by $$\theta = 1 - e^{-\epsilon C T(t)}, \tag{3}$$

where
 $\epsilon$ = molar absorptivity of the fluorescent material (having the dimensions, for example, of liters/mole-cm),
 C = concentration of the fluorescent material in the resist (having the dimensions of moles/liter), and
 T(t) = thickness of the resist (in cm) at time t.
Thus, $$N = P \cdot [1 - e^{-\epsilon C T(t)}] \cdot \eta_f \cdot \eta_c \cdot \Delta t. \tag{4}$$

If the concentration of the fluorescent material, C, is sufficiently small so that $\epsilon C T(t)$ is small compared to 1.0 (as is often, but not always, the case in the practice of the invention), then the exponential function in Equations (3) and (4) is approximately given by $$e^{-\epsilon C T(t)} \approx 1 - \epsilon C T(t).$$

Therefore, $$\theta \approx \epsilon C T(t),$$

and $$N \approx P \cdot [\epsilon C T(t)] \cdot \eta_f \cdot \eta_c \cdot \Delta t. \tag{5}$$

As is evident from Equations (4) and (5), the detected fluorescence signal is a function of the thickness, T, of the resist. That is, as T(t) decreases during etching, the fluorescence signal, N, decreases. Consequently, the etch depth of the resist is readily monitored. But the photodetector generally detects not only the fluorescence signal, N, but also a background signal, $N_b$, (due, for example, to reflections of the fluorescence-inducing energy onto the photodetector). Near the etch end point, the background signal, $N_b$, is generally larger than the fluorescence signal, N, and thus the etch end point (the cessation of fluorescence) is signified not by the disappearance of the detected signal, but by a sharp change in the slope of the detected signal (the slope becomes zero as shown, for example, in FIG. 4). The sharp change in slope is readily detected and thus the etch end point is accurately determined.

The one factor which ultimately limits the signal resolution of any photodetector is shot-noise (in this regard see, e.g., *American Institute of Physics Handbook,* supra, p. 6-253), which is equal to the square root of the detected signal (the square root of the total number of electrons counted during each time interval, $\Delta t$). Because the background signal, $N_b$, is generally larger than the detected fluorescence signal, N, near the etch end point, the shot-noise associated with the former is generally larger than the shot-noise associated with the latter, near the etch end point. If the shot-noise associated with the background signal ($\sqrt{N_b}$) predominates over all other sources of noise, then it has been found that the error in the determination of etch end point in the inventive each monitoring technique, expressed as an equivalent SCM thickness, $\delta T$, is approximately given by $$dT \approx \frac{T(t)}{N(t)} \sqrt{N_b}. \tag{6}$$

In Equation (6), T(t) denotes the thickness of the SCM at time t, and N(t) denotes the corresponding detected fluorescence signal at time t. Generally, Equation (6) is evaluated at time t=0, before etching begins, and thus $$dT \approx \frac{T(t=0)}{N(t=0)} \sqrt{N_b}. \tag{7}$$

As is evident from Equation (7), $\delta T$ is inversely proportional to the initial signal level N(t=0). Because N(t=0) is directly proportional to the initial absorption fraction, $\theta$, and the quantum efficiency of the fluorescent material, $\eta_f$, both a high absorption fraction and a high quantum efficiency are desirable in order to achieve a large initial signal level, and thus a small $\delta T$.

In choosing a fluorescent material (for a particular SCM) in order to determine etch end point, an important consideration is the achievement of a small end point error, $\delta T$. But, if the SCM is, for example, a resist which is to be used to pattern a substrate, then an equally important consideration is that the chosen fluorescent material should be compatible with the resist and with the procedures used to expose and develop the resist. A fluorescent material is compatible with a resist if the fluorescence-inducing energy, and the resulting fluorescence, do not significantly affect the solubility of the resist. If solubility is, for example, increased by the fluorescence-inducing energy, then the portion of the resist subjected to the fluorescence-inducing energy will etch more quickly than the remainder of the resist, and thus the etch end point, as measured using the inventive technique, will not be indicative of the etch end point of the rest of the resist. Moreover, the energy used to expose the resist should not significantly adversely affect the fluorescent material, e.g., break the molecular bonds of the fluorescent material, effectively reducing the concentration of the fluorescent material (and thus increasing $\delta T$). In addition, a fluorescent material is compatible with the procedures used to expose and develop the resist provided the fluorescent material does not significantly reduce the sensitivity of the resist to the exposing energy and does not adversely affect the etching characteristics of the resist. These compatibility requirements are generally met only at low concentrations of the fluorescent material, typically no more than about 2-3 percent (by weight).

A procedure for choosing a fluorescent material (for a particular resist) which meets the above-described compatibility requirements, and which permits etch end point to be accurately determined (using conventional sources of fluorescence-inducing energies and conventional photodetectors), has been developed. This exemplary procedure has been found to be so effective that suitable fluorescent materials (for particular resists) are readily found which permit etch end point to be detected to within an error (expressed as an equivalent resist thickness, $\delta T$) smaller than about 100 Angstroms, smaller even than about 10 Angstroms, and potentially (theoretically) even smaller than about 0.1 Angstroms. (While there is no such thing as a physical layer of material whose thickness is less than 0.1 Angstroms, such a thickness represents, for example, the average thickness of a monomolecular layer of material, some of whose molecules have been removed.) This procedure is as follows.

The first step in the inventive exemplary procedure is to choose one or more fluorescent materials which do not include inorganic materials. Fluorescent materials which include inorganic materials, while not precluded, are undesirable because inorganic materials are often not readily etched during the etching (development) of resists.

The second step in the inventive exemplary procedure is to select fluorescent materials (which do not include inorganic materials) whose fluorescence-inducing energy, and resulting fluorescence, will not significantly affect the solubility of the resist (under consideration) during resist etching (development). This is done, for example, by measuring (using conventional techniques and typical fluorescence-inducing beam powers of, for example, about 1 milliwatt) how large a dose (in joules/cm$^2$), from each of the fluorescence-inducing and fluorescence energies, is needed to fully expose control samples of the resist (through their thicknesses). By estimating the amount of time required to etch (develop) the resist through its thickness, estimates are then made of the dose the resist will receive during etching from each of the fluorescence-inducing and fluorescence energies. Based on these estimates, only those fluorescent materials are chosen whose fluorescence-inducing and fluorescence energies will subject the resist, during etching, to an exposure does which is small compared to the dose required to expose the resist through its thickness. Preferably, the exposure dose should be no greater than about 2 percent of the dose required to expose the resist through its thickness. While greater doses are not precluded, exposure doses greater than about 2 percent undesirably increase the error in the determination of etch end point. (The area of the resist subjected to the fluorescence-inducing and fluorescence energies becomes, for example, more solubilized than the areas not subjected to these energies, and thus this area etches more quickly than the other areas. Consequently, the etch end point will be in error.)

The third step in the inventive exemplary procedure is to eliminate those fluorescent materials which cannot be uniformly physically mixed with the resist at a concentration of at least 0.001 percent (by weight). Preferably, the fluorescent materials should uniformly mix with the resist at a concentration of at least about 1 percent (by weight). Concentrations smaller than about 0.001 percent, while not precluded, are undesirable because they generally yield end point errors, $\delta T$, larger than about 100 Angstroms. (At typical fluorescence-inducing beam powers of, for example, about 1 milliwatt, and at typical background levels, the corresponding quantum efficiencies and absorption fractions are generally not high enough to offset concentrations smaller than about 0.001 percent, in Equation (7), to produce a $\delta T$ of about 100 Angstroms.) Typically, a fluorescent material is mixed with the resist by depositing the fluorescent material (generally in powder form) into the resist solution (which includes the resist and a solvent). When the resist is, for example, spin-coated onto a substrate, the solvent evaporates and the fluorescent material mixes with the resist. A fluorescent material is uniformly physically mixed with a resist, for purposes of the invention, provided that any crystallites which form in the resist (small aggregations of fluorescent material, readily seen in optical or scanning electron micrographs) are smaller than about 1 $\mu$m in diameter and are spaced apart by at least 100 $\mu$m. Crystallites larger than about 1 $\mu$m and/or crystallite spacings smaller than about 100 $\mu$m often result in a loss of local detail during resist exposure and development.

The fourth step in the inventive exemplary procedure is to select from among the fluorescent materials chosen above, those which fluoresce brightly, i.e., have quantum efficiencies, $\eta_f$, greater than about 0.01 percent (when mixed with the resist at concentrations of at least 0.001 percent). (The quantum efficiencies, $\eta_f$, of the fluorescent materials are often altered, e.g., reduced, when mixed with resists, the degree of alteration often being dependent on the concentration of the fluorescent material in the resist.) While fluorescent materials having quantum efficiencies smaller than about 0.01 percent are not precluded, such materials are undesirable because they generally yield errors ($\delta T$) in etch end point which are larger than about 100 Angstroms.

The fifth step in the inventive exemplary procedure is to select those fluorescent materials which (when mixed with the resist at concentrations of at least 0.001 percent) yield resist films whose absorption fractions, $\theta$, expressed as percentages, are greater than about 0.01 percent but less than about 50 percent. Absorption fractions are readily measured by, for example, depositing control samples of the resist, doped with the fluorescent material (at concentrations of at least 0.001 percent), onto a substrate whose transparency to the fluorescence-inducing energy is known. By subjecting the control samples to the fluorescence-inducing energies, and measuring the transmitted fluorescence-inducing energies, the absorption fractions are readily determined. Fluorescent materials which yield resist films whose absorption fractions, $\theta$, are smaller than about 0.01 percent, while not precluded, are undesirable because they generally produce end point errors, $\delta T$, larger than about 100 Angstroms. Fluorescent materials which yield absorption fractions, $\theta$, greater than about 50 percent, while not precluded, are undesirable because they tend to be highly absorptive of both the fluorescence-inducing energies and the energies used to expose the resist. Thus, during exposure, much of the exposure energy is absorbed by fluorescent material near the top of the resist film, leaving the bottom of the resist film underexposed.

During the sixth step of the exemplary procedure (after the background level, $N_b$, has been measured), Equation (7) is used to determine the concentrations, C, of the fluorescent materials selected above, needed to achieve the desired end point error, $\delta T$. The various fluorescent materials under consideration are then mixed into control samples of the resist at the above-computed concentrations. Those fluorescent materials which do not uniformly mix (as defined above) with the resist, at the computed concentration levels, and which do not exhibit the desired levels of $\theta$ and $\eta_f$ (at the computed concentration levels), are eliminated.

The control samples not eliminated in the sixth step are then subjected to the energy used to expose the resist. The degree to which the molecular bonds of the fluorescent materials in the control samples are broken, thus effectively reducing the concentrations of the fluorescent materials, is determined by subjecting each control sample (after exposure) to fluorescence-inducing energy and measuring the resulting fluorescence. If the effective concentration of a fluorescent material has been reduced (as measured by a reduction in fluorescence intensity), then this reduction is offset by increasing the initial concentration. The sixth step is then repeated at the increased concentrations.

Often, resists are subjected to various sources of heat, e.g., the heat generated during prebaking of the resist. This heat often causes some of the molecular bonds of a fluorescent material to be broken, effectively reducing the concentration of the fluorescent material, and thus reducing the intensity of the fluorescence. If this is the case (as determined by subjecting a control sample of the doped resist to the heat), then this reduction is offset by increasing the initial dopant concentration, as described above.

The fluorescence-inducing energy will often also break some of the molecular bonds of the fluorescent material, effectively reducing the concentration of the fluorescent material. This reduction is also offset by increasing the initial concentration, as described above.

Finally, the control samples which have survived the above steps are exposed and then etched (developed). The etching procedure often causes irreversible damage to the fluorescent materials, effectively reducing the concentrations of the fluorescent materials, and this is then offset, as described above.

If the SCM is not to be exposed, as in the planarization etch process, then that aspect of the above procedure relating to exposure is eliminated.

To repeat, the above-described procedure is useful for selecting suitable fluorescent materials which will enable the etch end point of a particular SCM to be accurately determined. Etch end point errors smaller than about 100 Angstroms are readily achieved provided the concentration (in the SCM) of a (compatible) fluorescent material is greater than about 0.001 percent (by weight). In addition, the quantum efficiency of the fluorescent material (in the SCM) should be greater than about 0.01 percent, and the fluorescent material should yield an SCM film whose absorption fraction is greater than about 0.01 percent but smaller than about 50 percent.

Among the fluorescent materials which have been found useful (using the above-described procedure) for detecting the etch end point of SCMs is 4-dicyanomethylene-2-methyl-6-p-diethylaminostyryl-4H-pyran (DCM). DCM absorbs (fluorescence-inducing) electromagnetic radiation in a broadband centered at about 500 nm, and fluoresces in a broadband centered at about 590 nm.

One of the resists with which DCM is compatible is the commercially available positive photoresist sold under the trade name AZ2400 by the Shipley Corporation of Newton, Mass. AZ2400 is typically exposed by light at wavelengths of about 365, 404, and 436 nm, and is, for example, etched (developed) in an $O_2$ plasma. DCM is compatible with these exposure and etching procedures.

EXAMPLE 1

The plasma etching of the commercial positive photoresist AZ2400 was monitored by initially saturating a commercial solution of AZ2400 (the photoresist was dissolved in a solvent), purchased from the Shipley Corporation of Newton, Mass., with the fluorescent material DCM, purchased (in powder form) from the Exciton Chemical Company of Dayton, Ohio. The concentration of the DCM in the AZ2400 solution was about 1 percent by weight. The solution was passed through a 0.2 $\mu$m filter, spun onto a 4-inch silicon wafer at about 3000 rpm, and baked under vacuum at about 120° C. for about 15 minutes. The thickness of the resulting photoresist film was measured with a Dektak II profilometer and found to be about 1.30 $\mu$m. The quantum efficiency, $\eta_f$, of the DCM in the AZ2400 was estimated, by visual inspection (fluorescence-inducing light was shined on the AZ2400, and the resulting fluorescence was visually observed) to be in the range 0.1 to 1.0.

The absorption fraction, $\theta$ ($\theta = 1 - e^{-\epsilon CT}$), of the DCM-doped photoresist film was measured by forming such a film on a glass substrate and shining fluorescence-inducing light, in the wavelength range 480–520 nm, through the photoresist-covered glass substrate. By measuring the intensity of the transmitted light, the absorption fraction, $\theta$, was determined to be 0.50±0.01, and thus $\epsilon CT$ was calculated to be 0.69. Because DCM has a molar absorptivity, $\epsilon$, equal to $4.4 \times 10^4$ liters/mole-cm (at 500 nm), and because the thickness, T, was measured to be 1.30 $\mu$m, it follows that the concentration, C, of the DCM in the AZ2400 was about 2.4 percent (by weight). After the absorption fraction, $\theta$, was measured, the silicon wafer (covered with the DCM-doped AZ2400 photoresist) was mounted on the grounded electrode of a parallel-plate plasma etching machine.

The optical system used to induce fluorescence, and to monitor the etching of the DCM-doped photoresist film spun onto the silicon wafer, is shown in FIG. 3. As schematically depicted, the optical system 25 included a 100 W Hg arc lamp 28 whose output was focused by lenses 30 onto an aperture 40 where light in the wavelength band 480–520 nm (the fluorescence-inducing energy) was isolated by interference filter 50 and modulated by chopper 60. The modulated light was focused by lenses 70 onto a fused-silica optical fiber bundle 80, which extended through an aperture into the plasma etching machine (the optical fiber bundle 80 is not etched by the plasma). The fiber bundle 80 was used to illuminate an area of about 2 cm$^2$ on the surface of the photoresist-covered silicon wafer during etching. The optical fiber bundle 80 also served to collect and transmit some of the fluorescence (emitted by the DCM during etching) back to a dichroic beam splitter 90 where the fluorescence was reflected onto a lens 100. The lens 100 focused the fluorescence onto an RCA Model 4526 photomultiplier tube (PMT) 130 through an aperture 120 and red-glass filter 110. The aperture 120 served to exclude stray light, and the red-glass filter 110 served to isolate the DCM fluorescence from the fluorescence-inducing light and the white light emitted by the plasma (during etching).

The optical system 25 also included a lock-in amplifier 140 for phase-sensitive detection of the PMT signal. In order to normalize against fluctuations in arc-lamp power, the fluorescence signal was divided by a reference signal derived from the stray reflection of the fluorescence-inducing light off the dichroic beam splitter 90 into a second optical fiber bundle 150 and photodiode 160.

Throughout the etching procedure, the end of the fiber bundle 80 was maintained about 15 mm from the silicon wafer, at an angle of about 50 degrees from the vertical. Placing the end of the fiber closer to the wafer interfered with etching.

FIG. 4 shows a recording of the normalized fluorescence signal detected during etching of the DCM-doped photoresist. Initially, a background level was recorded by placing a bare silicon wafer in the field of view of the fiber 80 (which was emitting fluorescence-inducing energy). At t$\dot{=}$4 mins, the photoresist-covered wafer was moved into place, causing a large increase in the detected signal. From the ratio of this detected signal level (which corresponds to a resist film of thickness equal to 1.3 $\mu$m) to the background level, it was calculated that the background level was equivalent to the signal from a resist film having a thickness of about 600 Angstroms.

Between t$\dot{=}$4 mins and t$\dot{=}$9 mins, the vacuum system was closed and pumped out. At t$\dot{=}$9 mins, O$_2$ gas was admitted to the plasma etching chamber at a pressure of about 7 microns and a flow rate of 14 sccm. The detected signal drifted slowly upward during these procedures. From past experience, it was known that the signal always stabilized with time. Without waiting for complete stability, and at t$\dot{=}$15 mins, a plasma discharge was initiated by applying 100 watts of rf (13.56 MHz) power to the power electrode of the plasma etching machine, which electrode was spaced about 20 cm from the grounded electrode bearing the wafer. The initial sharp drop in the recorded signal (see FIG. 4) was due to heating of the photoresist. From previous experience, it was known that the temperature of the photoresist stabilized at about 50° C. within 3–4 minutes. Thereafter, as is evident in FIG. 4, the signal dropped as the photoresist film was etched away.

The periodic modulation seen in FIG. 4 was due to interference between fluorescence emitted in the direction of the optical fiber and light reflected by the silicon wafer. In addition, if a smooth curve is drawn through the means of the modulations in FIG. 4, a slight convex curvature becomes apparent. This convex curvature is due to the fact that $\epsilon CT(t=0)$ was not small ($\epsilon CT(t=0) = 0.69$), and thus $\theta$ was not linearly proportional to T, and consequently the (average or mean) signal, N, was not linearly proportional to T.

The etch end point in FIG. 4 is clearly visible as an abrupt change in slope at t$\dot{=}$37 mins. The error in etch end point determination was not, however, primarily due to the shot-noise associated with the background signal. Rather, the accuracy in the determination of etch end point was limited by the 3-second response time of the electronics employed in the detector system. Because the thickness of the photoresist (1.3 $\mu$m) was etched in 21 mins, it follows that the average etch rate was about 10 Angstroms/sec. Thus, the 3-second response time limitation implies that the error in etch end point, expressed as an equivalent resist thickness, was (10 Angstroms/sec)(3 sec) = 30 Angstroms.

If the shot-noise in the background signal had been the limiting factor, then the error in the determination of etch end point, expressed as an equivalent resist thickness, would have been (theoretically) even less than about 0.1 Angstroms. This follows from the fact that the power, P, of the fluorescence-inducing energy incident on the area of the resist (2 cm$^2$) subjected to this energy was P $\approx 10^{-3}$ watts $\approx 3.1 \times 10^{15}$ photons/sec (as estimated from the total power output of the Hg arc lamp and the fraction of this power transmitted by the fiber bundle). In addition, conservative estimates for $\eta_f$ and f suggest that $\eta_f \approx 0.5$ and f $\approx 10^{-4}$. Moreover, calculations based upon the manufacturer's specifications (for the PM tube) indicate that $\eta_c \approx 0.1$. Thus, because it is known that $\theta = 0.5$ and $\Delta t = 3$ sec, Equation (4) indicates that N(t=0) (the number of electrons corresponding to the 1.3 $\mu$m film) was approximately $2.3 \times 10^{10}$. As noted above, the background level, N$_b$, was equivalent to the fluorescence signal from a film having a thickness of about 600 Angstroms, and therefore $$N_b = (600 \text{ Angstroms}/1.3 \text{ }\mu\text{m}) \times 2.3 \times 10^{10}$$
$$= 1.1 \times 10^9.$$

Consequently, from Equation (7), it follows that (theoretically)

$$dT = \frac{T(t=0)}{N(t=0)} \sqrt{N_b} = \frac{(1.3 \text{ }\mu\text{m})(1.1 \times 10^9)^{\frac{1}{2}}}{2.3 \times 10^{10}}$$
$$= 0.019 \text{ Angstroms.}$$

EXAMPLE 2

A sample of AZ2400 photoresist, doped with DCM, was prepared as in Example 1, and spin-deposited (as in Example 1) onto a glass substrate whose index of refraction was approximately the same as that of the photoresist film (the index of refraction was about 1.5). The resist was then etched, and the etching monitored, as in Example 1. A recording of the normalized fluorescence signal during etching of the resist is shown in FIG. 5(a). The interference ripples seen in FIG. 4 are substantially reduced in FIG. 5(a) because the mismatch in the optical properties (indices of refraction) between the photoresist film and the substrate had been substantially eliminated.

EXAMPLE 3

A sample of AZ2400 photoresist, doped with DCM, was prepared and spin-deposited onto a glass substrate, as in Example 2, except that the DCM concentration was reduced by a factor of 4 (and thus $\theta$ was reduced by a factor of 4). This film was then etched, and the etching monitored, as in Example 2. For such a film, Equation (5) is applicable and predicts that fluorescence intensity is linearly proportional to film thickness. FIG. 5(b), which is a recording of the fluorescence signal detected during the etching, shows this to be the case.

EXAMPLE 4

A film of AZ2400 photoresist, doped with DCM, was prepared and spin-deposited onto a glass substrate, as in Example 3. The film was then etched, and the etching monitored, as in Example 3, except that the applied rf power was reduced by a factor of 2. The change in the slope of the curve shown in FIG. 5(c), which is a recording of the fluorescence signal detected during etching, reflects the reduction in etch rate.

What is claimed is:

1. A method for fabricating a device, said method comprising the steps of:
    forming a sacrificial coating material on a substrate; and
    etching at least a part of said material,
Characterized In That
    said material includes fluorescent material, and
    said method further comprises the step of monitoring the etching of said sacrificial coating material by subjecting at least a portion of said part to a form of energy which induces unetched fluorescent material within said portion to fluoresce, and sensing the resulting fluorescence.

2. The method of claim 1 wherein said substrate includes a non-planar surface.

3. The method of claim 1 wherein said sacrificial coating material includes a first layer of material deposited onto said substrate, and a second layer of material deposited onto said first layer.

4. The method of claim 3 wherein said sacrificial coating material further includes a third layer of material deposited onto said second layer.

5. The method of claim 4 wherein said first layer of material includes said fluorescent material.

6. The method of claim 1 or claim 2 wherein said etching is discontinued when the sensed fluorescence substantially ceases.

7. The method of claim 5 wherein said etching step includes the steps of successively etching said third and second layers, the etching of said second layer being discontinued when the sensed fluorescence is first observed to substantially diminish.

8. The method of claim 5 or 7 wherein said etching step includes the step of etching said first layer, the etching of said first layer being discontinued when the sensed fluorescence substantially ceases.

9. The method of claim 6 wherein the detected time of cessation of said fluorescence differs from the true etch end point of said sacrificial coating material by an equivalent thickness of said sacrificial coating material less than about 100 Angstroms.

10. The method of claim 6 wherein the detected time of cessation of said fluorescence differs from the true etch end point of said sacrificial coating material by an equivalent thickness of said sacrificial coating material less than about 10 Angstroms.

11. The method of claim 8 wherein the detected time of cessation of said fluorescence differs from the true etch end point of said first layer by an equivalent thickness of said first layer less than about 100 Angstroms.

12. The method of claim 8 wherein the detected time of cessation of said fluorescence differs from the true etch end point of said first layer by an equivalent thickness of said first layer less than about 10 Angstroms.

13. The method of claim 1 wherein the concentration of said fluorescent material in said sacrificial coating material is greater than about 0.001 percent.

14. The method of claim 1 wherein the quantum efficiency of said fluorescent material, in said sacrificial coating material, is greater than about 0.01 percent.

15. The method of claim 1 wherein said sacrificial coating material absorbs more than about 0.01 percent, but less than about 50 percent, of the incident fluorescence-inducing energy.

16. The method of claim 1 wherein said fluorescent material includes 4-dicyanomethylene-2-methyl-6-p-diethylaminostyryl-4H-pyran.

* * * * *